United States Patent [19]

Sims

[11] Patent Number: 4,846,809
[45] Date of Patent: Jul. 11, 1989

[54] NEEDLE TIP PROTECTIVE DEVICE

[76] Inventor: Winifred Sims, 4526 Mount Vernon Dr., Los Angeles, Calif. 90043

[21] Appl. No.: 161,486

[22] Filed: Feb. 29, 1988

[51] Int. Cl.⁴ ............................................. A61M 5/32
[52] U.S. Cl. .................................... 604/198; 604/263
[58] Field of Search ............... 604/198, 263, 187, 192, 604/163

[56] References Cited

U.S. PATENT DOCUMENTS

2,847,995  8/1958  Adams ................................. 604/198
4,564,054  1/1986  Gustavsson ..................... 604/198 X Primary Examiner—John D. Yasko

[57] ABSTRACT

A needle tip protective device which is universally adapted for use with a large number of needle supports including syringe needles, Vacutainer apparatus and intravenous catheter placement needle and intravenous catheter combinations without requiring any alteration or modification of the needle support. The needle tip protective device comprises a collapsable sleeve which is disposed about the shank of the needle and a protective cap located at one end which surrounds and encloses the sharp tip point of the needle. A sealing member is located within the cap and effectively encloses the sharp tip point of the needle within the cap until the needle is pushed through the sealing member.

19 Claims, 3 Drawing Sheets

NEEDLE TIP PROTECTIVE DEVICE

BACKGROUND OF THE INVENTION

1. Field of the Invention

This invention relates in general to certain new and useful improvements in needle tip protective devices, and more particularly, to needle tip protective devices which are capable of being used with a large number of supports without requirement of a special support construction and usually without special attachment means therefor.

2. Brief Description of the Prior Art

For many years the medical profession has utilized a variety of medical devices for puncturing the skin to enable delivery or removal of fluid from a patient's body and which are generally referred to as "needles". The structure of such needles has varied substantially depending on treatment indicated. One type of needle construction, with which the needle tip protective device may be used, is generally referred to as hypodermic needles and which comprises a reservoir suitable for accommodating fluid. This hypodermic needle is also equipped with movable piston utilized to expel the fluid from the reservoir through an aperture in the reservoir. In the most common construction, the reservoir is an elongate cylinder having a slideable push rod coupled to the piston and an aperture at the opposite or distal end. An elongate hollow cylindrical needle is sealingly coupled to the reservoir end and the aperture therein and terminates in a sharp point configured to readily puncture the patient's skin.

In normal use, a quantity of an infusion fluid is drawn into the reservoir of the hypodermic needle after which air is expelled by discharging a small amount of the infusion fluid out through the needle. Thereafter, the needle point is inserted through the skin and, in most cases the blood vessel wall of the patient. The infusion fluid is then expelled out through the needle by movement of the push rod and piston.

In addition to the use of hypodermic needles for injection of substances into the patient, a similar device often referred to as a Vacutainer may be employed to perform the function of withdrawing a fluid sample, such as blood, from the patient. The Vacutainer comprises a housing sized to receive a blood or other body fluid tube and which is provided with a stopper on the end thereof. Moreover, the tube is under a vacuum. A double pointed needle is connected to the housing with one sharp pointed tip adapted for insertion into a patient's body and typically into a vein or artery. The other tip extends into the housing and arranged to extend through the stopper when the sample tube is introduced into the housing. In essence, when the needle portion of the Vacutainer is inserted into the patient and the opposite needle end communicates with the sample tube, the vacuum within the sample tube draws the desired body fluid into the tube. Once the desired quantity of body fluid has been drawn into the tube, the needle is removed.

Another basic type of needle construction utilized by medical practitioners is referred to as an intravenous catheter and intravenous catheter placement needle combination. In general, these intravenous catheter systems comprise two basic system parts, the intravenous catheter itself and an intravenous catheter placement needle. The intravenous catheter comprises a housing which supports an outwardly extending generally thin hollow tube. The intravenous catheter is configured to receive an intravenous catheter placement needle similar to, but of generally thinner cross-section and of shorter length, than the hypodermic needle. The intravenous catheter and intravenous catheter placement needle are constructed to permit the intravenous catheter placement needle to be inserted through the intravenous catheter housing and extend through and beyond the intravenous catheter tube. When so assembled, the intravenous catheter and intravenous catheter placement needle form a single unit which terminates in the outwardly extending intravenous catheter placement needle having a sharp piercing point and a surrounding intravenous catheter tube.

In use, the intravenous catheter and intravenous catheter placement needle assembly are inserted into the patient's blood vessel by inserting the intravenous catheter placement needle point and intravenous catheter tube end through the patient's skin and blood vessel walls similar to a hypodermic needle or Vacutainer insertion. In contrast to a hypodermic needle use however, the intravenous catheter placement needle is then withdrawn from the intravenous catheter assembly leaving the intravenous catheter tube within the patient's blood vessel. Once the intravenous catheter placement needle is withdrawn, a tube is attached to the intravenous catheter in a sealing manner and is coupled to a supply of the fluid which is to be introduced into the patient's system.

In accordance with modern medical technology, essentially all needle constructions are sterilized and maintained in a sterile condition prior to their use with patient. In most instances, the majority of needles utilized today by modern medical practitioners are actually manufactured, sterilized, wrapped in a sterile package and used a single time and discarded after use. Since the needles are initially sterile, their handling during use by medical practitioners prior to any contact with the patient does not represent any substantial health hazard to the practitioner. However, while the use of sterile needles provides protection to the patients during the time the needles are used, the contamination of the needles by the patient's system during use transforms the previously sterile needles into a potentially dangerous object for the medical professional. Because the needles are generally manufactured of a high quality surgical-type steel, they readily maintain their sharp pointed condition after use. As a result, a potential exists for inadvertent or accidental piercing of the skin of the medical professional handling the needles subsequent to use on a patient.

Because many diseases, such as hepatitis or acquired immune deficiency syndrome (AIDS), etc., are readily transferrable by inadvertent or accidental puncturing of the user's skin with a contaminated needle, a substantial danger is presented to members of the medical professional through use of such needles. This problem is exacerbated by the environment in which the medical professionals function, in that frequently needles are used and handled in distracting or stressful environments, and in some instances in emergency situations.

To meet this problem and reduce the danger presented to medical professionals by the use of needles, manufacturers have provided various needle covering caps and similar structures with the intent that the needle cap be replaced by the professional immediately after withdrawing the needle from the patient. While such replacement caps and the like do provide protection of the professional by covering the needle point, it has been found that the medical professional often fails to take the time to replace the cap in order to protect themselves or others from inadvertent skin piercing or scratching. In addition, the very act of returning the needle cap to the needle in itself often presents a substantial danger of piercing the medical professional's skin with a potentially contaminating result.

One of the significant problems with most of the commercially available needle tip protective devices is the fact that the protective device must be specially constructed for use with a particular needle support such as a particular hypodermic needle or intravenous catheter system or the like. Otherwise, most needle apparatus manufacturers must specifically design their needle apparatus in such manner as to accommodate and be used with a conventional needle tip protective device. There are generally no commercially available needle tip protective devices which are universally usable with a large number of syringes. More specifically, there are no commercially available needle tip protective devices which are usable with intravenous catheter placement needles, hypodermic needles or Vacutainer devices and which do not require a special construction or adapter for use with each.

There have been several proposed needle tip protective devices for use in shielding needles on various supports, but each of these proposed protective devices suffers from one or more of the limitations as mentioned above. U.S. Pat. No. 3,134,380 to Armao discloses a needle tip protective device which is used with a hypodermic needle. However, in the Armao patent, the device itself is constructed only for a particular type of hypodermic needle and must be used only with a syringe having a specific hub size. Otherwise, in order to accommodate different sized syringes, numerous needle tip protective devices must be provided in accordance with the Armao construction. In addition, in the Armao construction, the cap which covers the distal end of the needle having the sharp point is intended to be removable such that removing and replacement of the cap is required.

U.S. Pat. No. 3,354,881 to Bloch also discloses a compressable device adapted to extend over the shank of a needle and is adapted with a rubber septa at each of the opposite ends and which is designed to be placed over and surround a hypodermic needle. However, this device is intended to be removable from the needle and is not disposable with the needle. Moreover, a device of the type taught in the Bloch patent is intended primarily for re-usable needles.

U.S. Pat. No. 4,139,009 to Alvarez also discloses a needle tip protective device and comprises a permanently attached cover surrounding the needle with a number of elastically resilient arms which extend along the length of the needle. These arms are constructed so as to bow outwardly from the shank of the needle when the needle is pressed against the skin of the patient. Moreover, there is no separately removable cap covering the tip of the needle. In addition, and in the Alvarez construction, the needle must be attached directly to a hub portion of a syringe which again limits the universality of use.

U.S. Pat. No. 4,660,570 to Dombrowski also discloses a needle tip protective device extending over a hypodermic needle and which includes a membrane extending over the sharp point of the needle. This membrane is intended to be pressed against the skin such that the needle extends through the membrane and through the skin of the patient in use.

U.S Pat. No. 4,650,468 to Jennings, Jr. also discloses a needle tip protective device for use with a hypodermic needle and which includes a sleeve concentrically disposed about the needle shank. The Jennings, Jr. construction also utilizes a safety shield at one end with a rubber membrane extending across an opening in the shield and which is adapted to be pierced by the sharp point of the needle when in use.

There are other U.S. patents which show needle protective devices such as the Brunet U.S. Pat. No. 4,553,962, the White U.S. Pat. No. 2,876,770 and the Sagstetter et al U.S. Pat. No. 4,664,653, each of which do not overcome the numerous problems as mentioned above in connection with the prior art needle tip protective devices. As a result, there still remains a need for an easy to use, simple and effective needle tip protective device which is universally usable with a wide variety of hypodermic needles, Vacutainers and intravenous catheter placement needles and the like without requiring a special support or construction therefor.

OBJECTS OF THE INVENTION

It is, therefore, one of the primary objects of the present invention to provide a needle tip protective device which is capable of being used with a wide variety of needle supports without requiring a special support construction or adapter therefor.

It is another object of the present invention to provide needle tip protective device which is capable of being use with needle supports having different sizes and constructions and which attaches directly to the shank of a needle.

It is a further object of the present invention to provide a needle tip protective device of the type stated which can be constructed at a relatively low cost but which is highly efficient in operation and effective in use.

With the above and other objects in view, my invention resides in the novel features of form, construction, arrangement and combination of parts presently described and pointed out in the claims.

BRIEF SUMMARY OF THE DISCLOSURE

A needle tip protective device for use with a needle having a shank with a first end connected to a support and a second end having a sharp point capable of intravenous or intramuscular or subcutaneous insertion. The needle tip protective device comprises a resilient flexible sleeve which is capable of being disposed about the elongate shank of a needle and extends from the second end for at least the greater portion of the length of the shank toward the first end. The sleeve has an elongate central bore capable of receiving the elongate shank of the needle and is also capable of being concentrically disposed about the shank of the needle.

In accordance with the present invention, the sleeve has at least a portion proximate the first end of the needle and the bore thereof which has a diameter sufficient to snugly engage the outer wall above the needle and thereby retentively hold the protective device with respect to the needle and the support. This avoids the need of a special attachment means or other construction to attach the device to the support which holds the needle.

The needle tip protective device of the present invention also includes a cap secured to the second end of the sleeve and which is located to extend around and receive the second end of the needle. This cap has an enlarged opening through which the sharp point of the second end of the needle may extend.

A sealing member normally extends across the enlarged opening of the cap and thereby encloses the sharp point of the second end of the needle within the chamber surrounding the needle. This chamber is essentially formed by the central bore of the sleeve and the cap. Thus, the user of the needle tip protective device is protected from the sharp point of the second end of the needle. In addition, the sharp point is capable of extending through the sealing member when the needle is pushed against the skin surface. This will cause the sealing member to be pushed against the needle tip sharp point causing the needle to extend through the sealing member and thereby causing the sleeve to compress about the needle shank as a portion of the needle extends through the patient's skin.

In one embodiment of the invention, the sealing member may be a membrane which extends across the open end of the cap and is pierced by the sharp point of the needle. In another embodiment of the invention, the sealing member may be a plug which has a small diameter central aperture extending therethrough but which is sized to slidably receive the needle as the plug and sleeve are pushed upwardly about the shank of the needle when the latter is forced into a patient's skin.

This invention possesses many other advantages and has other purposes which may be made more clearly apparent from a consideration of the forms in which it may be embodied. These forms are shown in the drawings accompanying and forming a part of the present specification. They will now be described in detail for the purposes of illustrating the general principles of the invention, but it is to be understood that such detailed description is not to be taken in a limiting sense.

BRIEF DESCRIPTION OF THE DRAWINGS

Having thus described the invention in general terms, reference will now be made to the accompanying drawings in which:

DETAILED DESCRIPTION OF PREFERRED EMBODIMENTS

Figures 1, 2:
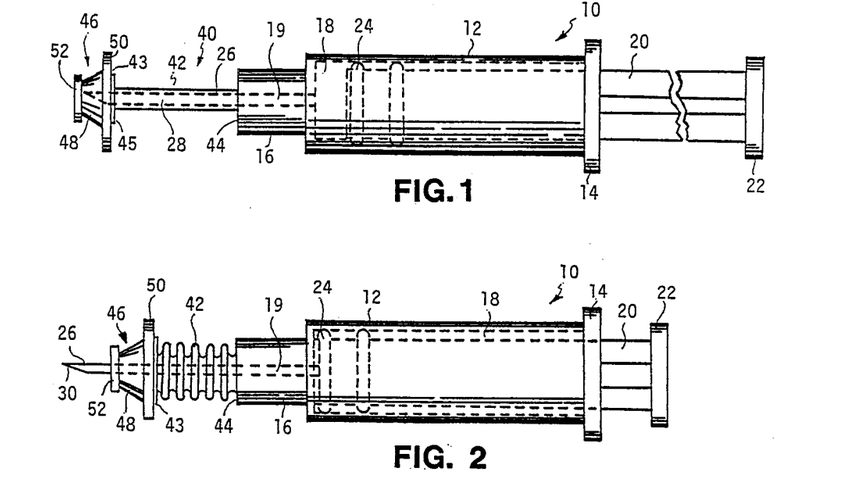
FIG. 1 is a side elevational view of a hypodermic needle showing a needle tip protective device of the present invention used thereon.
FIG. 2 is a side elevational view of a hypodermic needle having the needle tip protective device thereon, similar to FIG. 1, and showing the needle tip protective device in a collapsed or compressed condition with the needle tip extending therebeyond.

Referring now in more detail and by reference characters to the drawings, FIGS. 1 and 2 illustrate, in side elevational view, partially in section, a typical hypodermic needle 10 used with a needle tip protective device 40 constructed in accordance with and embodying the present invention. In order to more fully understand the principle an operation of the needle tip protective device 40, a portion of the hypodermic needle 10 will be briefly described.

The hypodermic needle 10 generally comprises an elongate generally cylindrical body 12 which functions as a cylinder and which includes an integrally formed circularly shaped flange 14 at one end thereof. At the other end, that is, the left-hand end, reference being made to FIG. 1 the body 12 is provided with a diametrically reduced hub 16. The body 12 is centrally bored to provide a fluid reservoir 18 which communicates with a cylindrically shaped fluid passage 19 formed in the hub 16, in the manner as illustrated in FIGS. 1-4 of the drawings.

Reciprocatively shiftable within the reservoir 18 is a conventional piston rod 20 having an enlarged handle 22 at its right-hand end, reference being made to FIGS. 1 and 2. The piston rod 20 is provided with a piston or so-called "plunger" 24 at its left-hand end, as also best illustrated in FIGS. 1 and 2 of the drawings. In accordance with this construction, if the piston 24 is pulled to the right-hand end, toward the flange 14, it will create a vacuum and draw a fluid into the reservoir 18. In like manner, if the piston 20 is pushed inwardly into the reservoir 18, the piston 20 will cause a discharge of any fluid contained in the reservoir 18.

In accordance with a conventional construction, the hypodermic needle 10 is provided with a generally metal cylindrically shaped tubular needle 26. This needle has a first end that is, the right-hand end, which is fixed within and rigidly secured to the hub 16. Moreover, the needle 26 has a central bore 28 which is in fluid communication with the bore in the hub 16 and hence, in fluid communication with the reservoir 18. Furthermore, the needle 26 includes a sharp-tipped point 30 at its second end, that is its left-hand end, reference again being made to FIGS. 3 and 4 of the drawings. The needle tip point 30 is sufficiently sharp so as to easily puncture and extend through a patient's skin and thereby contact a source of body fluid such as blood contained in a blood vessel of a body.

The needle tip protective device 40 of the present invention generally comprises a elongate cylindrically shaped sleeve 42 which is formed of a flexible and resilient material, such as a flexible and resilient plastic or rubber material. The sleeve 42 has a first end 44 which is generally disposed in close proximity to and preferably in engagement with the hub 16, in the manner as illustrated in FIGS. 1-4 of the drawings. The sleeve 42 also has a second end, that is a left-hand end 45, reference being made to FIGS. 1-4 of the drawings, which is connected to a cap 46. In this case the second end of the sleeve 42 is provided with a flanged portion 43 permanently secured to the cap 46, such as by means of an adhesive or other means for permanently sealing the cap to the sleeve 42. The protective cap 46 is also formed of either a hard plastic or hard rubber material and thus, the sleeve 42 may be heat sealed to the cap 46 in order to provide permanent bond between these two components.

The protective cap 46 is comprised of a tapered body portion 48 having an enlarged flange 50 at its right-hand end and a diametrically reduced flange 52 at its left-hand end. The cap 46 is also provided with a elongate central bore 54 which extends axially through the body portion 48 and which is in axial alignment and in fluid communication with the bore of the needle and hence, in fluid communication with the reservoir 18.

Figure 3:
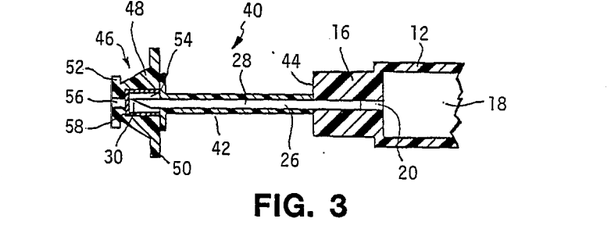
FIG. 3 is a fragmentary sectional view, similar to FIG. 1, and showing a portion of the needle tip protective device around the needle shank in the hypodermic needle of FIG. 1.
Figure 4:
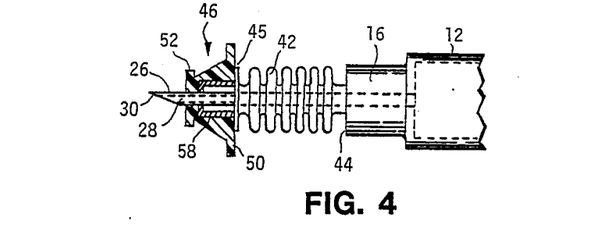
FIG. 4 is a fragmentary sectional view, similar to FIG. 3, and showing the needle tip protective device in the compressed condition with the needle tip extending through and beyond the protective cap therefore.

The central bore 54 of the cap 46 extends completely therethrough and is provided with an opening 56 at its left-hand end. A sealing membrane 58 extends across the aperture 56 in the manner as best illustrated in FIGS. 3 and 4 of the drawings. In this case, the sealing membrane 58 has somewhat of a cup-like configuration, as best illustrated in FIGS. 3 and 4 and fits snugly within the bore 54 formed in the body portion 48 of the cap 46. Moreover, the sealing membrane 58 may be fixed within the bore 54 by any suitable means and retentively held therein as for example, by an adhesive or the like.

In one of the preferred embodiments, the sleeve 42 has a length which is sufficient to extend between the first end adjacent the hub 16 to the second end at the cap 46 when the latter encloses the needle tip point within the cap. Moreover, the sleeve 42 should not be longer than the length of the needle shank since the sharp tipped point of the needle might otherwise accidentally penetrate the material of the sleeve 42 and thereby destroy the sterile environment maintained by the sleeve and the protective cap 46. Thus, a desirable length for the sleeve 42 is shown in the representation of FIG. 3 wherein the sharp tipped point is housed within the cap 46 and the sleeve extends from the cap 46 at the second end 45 to the hub 16 of the hypodermic needle at its first end.

By further reference to FIGS. 1 and 3 of the drawings, it can be observed that in a preferred embodiment, the sleeve 42 snugly fits around the shank of the needle and is retentively held thereon by frictional engagement. In this way, there is no need to permanently affix the sleeve to the hub 16 or to any other part of the hypodermic needle syringe or other support. In other words, merely inserting the needle through the sleeve 42 will cause a retentive engagement of the needle tip protective device with the hypodermic needle.

This construction completely eliminates the need for specially modifying the hypodermic needle or other support and for that matter, eliminates the need of specially designing the needle tip protective device so as to be used with any conventional support. Moreover, this construction eliminates the need for any special adapter for securing the needle tip protective device to the hypodermic needle syringe. It can be also observed that inasmuch as at least the right-hand end 44, that is the first end of the sleeve 42 is in frictional fluid-tight sealed engagement with the shank of the needle, there is a protective chamber formed around the shank of the needle by the sleeve 42 and the cap 46 along with the membrane 58.

As indicated previously, the sleeve 42 may be formed of a flexible and resilient material. However, it should be understood that anyone skilled in the art could select a variety of materials for fabricating the sleeve 42. In like manner, any of a number of materials could be used for fabricating the protective cap 46. The membrane 58 may also be formed of a thin sheet of any known membrane forming material. For this purpose, any sealing membrane capable of being pierced by the sharp tipped point of the needle could be employed.

One of the important properties of the sleeve 42 is its ability to wrinkle or fold into a plurality of convolutions as shown in FIG. 4 as it is moved along the shank of the needle axially with respect to the needle tip point in order to expose the needle tip point, as hereinafter described. The pair of flanges 50 and 52 on the body portion 48 of the cap 46 enables a user to easily and conveniently grasp the protective cap if required. In this way, the finger and thumb of the user would not be likely to be located in alignment with the aperture 56 where there is always a potential risk of being contacted by a needle if it should be inadvertently manipulated and caused to pierce the protective membrane 58.

By reference to FIGS. 2 and 4 of the drawings, it can be observed that in use, the flange 52 of the protective cap can be disposed against a patient's or subject's skin. By merely pushing on the hypodermic needle 10, the shank of the needle 26 will be moved to the left thereby causing the sharp tipped point of the needle to pierce the membrane 58. As this occurs, the sharp tipped point of the needle will also extend into the patient's skin. However, the force of the skin will push the protective cap 46 to the right, that is toward the body 12 of the hypodermic needle. As this occurs, the sleeve 42 will wrinkle and form convolutions as shown in FIGS. 2 and 4 thereby permitting the cap to move to the right that is, toward the syringe housing. In effect, it is the syringe body 12 which is being moved toward the cap as the shank of the needle 26 is extended into a patient's body.

After the plunger rod has been pushed into the reservoir 18 and any fluid therein injected into the body, the hypodermic needle 26, including the shank, is removed from the patient's body. As this occurs the elasticity within the protective sleeve 42 will cause the same to expand and thereby force the protective cap 46 to the left. Even if the sleeve 42 is not formed of a material which has sufficient elasticity to cause movement of the protective cap 46, the attendant or health professional utizilizing the hypodermic needle can merely grasp the cap 46 and move the same to the left so that the sharp tipped point is now protected within the cap 46. In this way, the entire needle device may be safely discarded.

It can be observed that the needle tip protective device of the present invention is highly effective for use with one-time disposable needles which can thereafter be discarded.

It should be noted that as mentioned above, the sleeve 42 is formed of a resilient material and thereby in effect, forms a spring-like structure when it is compressed and forms the convolutions as shown in FIGS. 2 and 4. In this position, it has a natural resilience and elasticity which exerts a counterforce against the protective cap 46. This resilient force of the sleeve is overcome and the cap remains in the position shown in FIG. 2 with the flange 52 resting against the patient's outer skin. However, as the needle is withdrawn from the patient's body, the resilient force and elasticity of the sleeve 42 forces the cap toward and over the needle point. When the needle has been completely withdrawn from the patient, the resilient force of the sleeve 42 returns the cap to its protective position, as shown in FIGS. 1 and 3 of the drawings.

The membrane is sufficiently thin but also formed with sufficient memory so that the opening formed by the penetrating needle point will tend to close after the needle tip has been retracted beyond the membrane. While the membrane will have been pierced and opened, there is at least a partial closing of the same so that the sharp tipped point of the needle is again enclosed.

Figure 5:
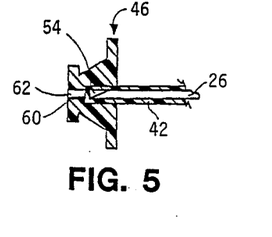
FIG. 5 is a fragmentary sectional view, somewhat similar to FIG. 3, and showing a modified form of needle tip protective device constructed in accordance with and embodying the present invention.
Figure 6:
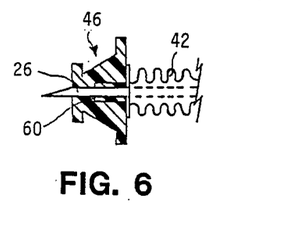
FIG. 6 is a fragmentary sectional view, somewhat similar to FIG. 5, and showing the needle tip protective device in the compressed condition with a portion of a needle tip point extending through the cap of the protective device.

FIGS. 5 and 6 illustrate an alternate embodiment of the needle tip protective device of the present invention which is similar to the needle tip protective device of FIGS. 1 and 4, except that the device of FIGS. 5 and 6 uses a modified form of sealing member. In the embodiment of FIGS. 5 and 6, the sleeve 42 is provided at its left end with an enclosing end wall 60. This end wall 60 serves as the puncturable membrane and thereby eliminates the need of a separate membrane. Moreover, the left-hand end of the sleeve 42 may be sealed within the bore 54 of the protective cap 46. The sharp pointed tip of the needle 26 remains within the protective cap until such time as the needle is actually used. When the cap 46 is pressed against the skin of a patient, the sleeve 42 will collapse as shown in FIGS. 2 and 4, and the needle will pass through the end wall 60 and extend through the patient's skin.

The needle tip protective device of the embodiment of FIGS. 5 and 6 utilizes a sleeve 42 which may be formed of any of the previously described materials. Moreover, the end wall 60 is tightly fitted within the bore 54 and completely covers the opening 56. This embodiment of the protective device is also constructed as a one-time disposable unit in the same manner as the needle tip protective devices of FIGS. 1 through 4 of the drawings.

Figure 7:
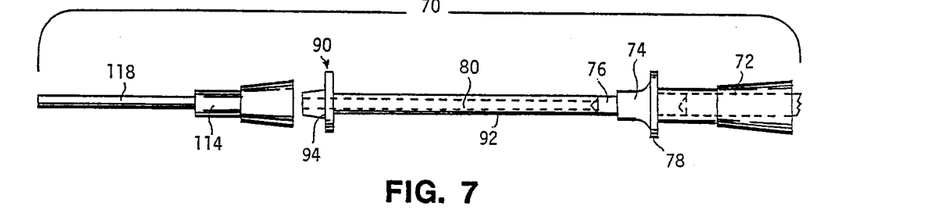
FIG. 7 is an exploded side elevational view, showing an intravenous catheter placement needle along with a needle tip protective device of the present invention used therewith.
Figure 8:
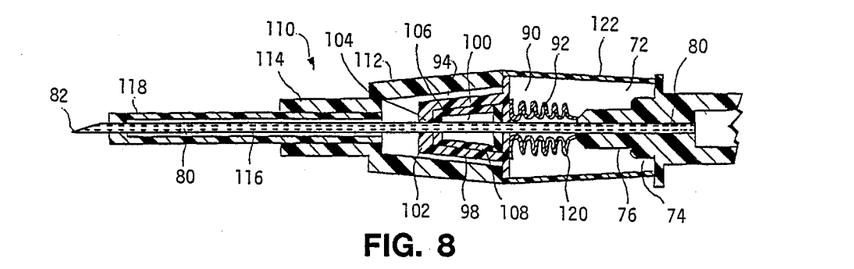
FIG. 8 is a fragmentary sectional view, somewhat similar to FIG. 7, and showing the needle tip protective device in the compressed condition with a portion of the needle tip extending through and beyond the cap of the protective device.

FIGS. 7 and 8 of the drawings set forth still another embodiment of a needle tip protective device which is configured to be used with an arrangement of a conventional intravenous catheter placement needle and intravenous catheter, as illustrated. In accordance with this construction, the arrangement of an intravenous catheter placement needle and intravenous catheter arrangement 70 comprises a generally cylindrical intravenous catheter assembly 72 having a cylindrical body 74 and diametrically reduced forwardly projecting hub 76. The body 74 also includes a generally circularly shaped outwardly extending flange 78. Extending forwardly from the hub 76 is an elongate intravenous catheter placement needle 80 which is generally of a tubular construction and which is also provided with a sharp pointed end 82. If required, the intravenous catheter placement needle could be of a longer than normal size.

FIG. 7 more fully illustrates the components of the arrangement 70 of the intravenous catheter placement needle along with a needle tip protective device shown in the partially exploded position. FIG. 8 is a sectional view more fully illustrating the position of the needle tip protective device on the intravenous catheter placement needle and in a position where the intravenous catheter placement needle and intravenous catheter are ready for insertion into a patient's skin. In accordance with the arrangement as illustrated in FIGS. 7 and 8, a needle tip protective device 90 is shown assembled on the intravenous catheter placement needle assembly 70. In this case, the needle tip protective device 90 comprises a cylindrically shaped transparent and resilient hollow plastic sleeve 92 which extends axially along and circumferentially about the shank of the intravenous catheter placement needle 80. Moreover, the innermost or right-hand end of the sleeve 92 may abut against the diametrically reduced hub 76 in the manner as illustrated in FIGS. 7 and 8 of the drawings. Preferably, the right-hand end of the sleeve 92 is sealed to the hub 76 by means of a rubber sealant which encloses the opening of this end and encompasses the needle tip anterior to the opening. This protective sleeve 92 is formed of essentially the same materials which are used in the formation of the protective sleeve 42 in the embodiments of FIGS. 1-4 of the drawings.

Fixedly secured to the left-hand or forward end of the sleeve 92 is a protective cap 94. Here again, the left-hand end of the sleeve 92 is secured to the cap 94 by a similar construction using a rubber sealant which encloses the left-hand end of the sleeve 92 within the cap 94. Further, the protective cap 94 is substantially similar in construction and operation to the protective cap 46 used in the embodiments of FIGS. 1-4 or the embodiments of FIGS. 5 and 6 of the drawings. The protective cap 94 is similarly formed of a somewhat tapered conically shaped body 98 having a central interior cavity 100. Moreover, the conically shaped body 98 is provided with a forwardly disposed relatively flat end wall 102 which is provided with a centrally located opening 104 sized to receive the shank of the intravenous catheter placement needle 80, in the manner as best illustrated in FIG. 8 of the drawings.

Located within the cavity 100 is a sealing member 106, which in this embodiment, comprises a rupturable membrane 108. However, it should be understood that an end wall on the sleeve, of the type illustrated in FIGS. 5 and 6, could also be used as the membrane in this embodiment of the invention.

A conventional intravenous catheter assembly 110 is provided for use with the assembly as illustrated in FIGS. 7 and 8 and this intravenous catheter arrangement 110 comprises a conically shaped body 112 which is disposed about and retentively held on the protective cap 94, in the manner as best illustrated in FIG. 8 of the drawings. The body 112 is also provided with a forwardly projecting cylindrically shaped hub 114 and which, in turn, has a central opening 116 to accommodate the shank of the intravenous catheter placement needle 80 extending therethrough. Fitted about the shank of the intravenous catheter placement needle is a conventional intravenous catheter tube 118. In this case, it can be observed that the inner end of the intravenous catheter tube terminates within the body 112 or otherwise, in the diametrically reduced hub 114 but is not securely held therein.

When fully assembled, and in the relative positions as shown, it can be observed that the protective sleeve 92 is compressed into a plurality of closely spaced wrinkles or convolutions 120. The unit will normally be packaged in the compressed state a shown in FIG. 8. It can be observed that with the intravenous catheter body 112 secured to the assembly, as illustrated, the protective cap 94 is pushed to the right which compresses the protective sleeve 92. Moreover, this causes the sharp tipped point 82 of the intravenous catheter placement needle to project through the membrane 108 and outwardly of the intravenous catheter body 112 and the intravenous catheter 118 as illustrated in FIG. 8. When in this position, the intravenous catheter placement needle and intravenous catheter are adapted for insertion into a patient's body.

When the intravenous catheter placement needle has been introduced into the patient's body, the intravenous catheter is positioned in a desired vessel, such as a blood vessel. The operator of the apparatus will know when there is a proper placement of the intravenous catheter by virtue of a blood return through the passage of the intravenous catheter placement needle and into the reservoir.

Once the insertion of the intravenous catheter placement needle 80 and the intravenous catheter tube 118 into the patient's body has been completed, the intravenous catheter body 112 may be affixed to the patient's body, generally by the use of an adhesive tape or like means. At this point, the intravenous catheter placement needle 80 may be withdrawn from he intravenous catheter 118 and the intravenous catheter body 112. As this occurs, the sleeve 120, which is in its compressed condition, would have sufficient elasticity to force the protective cap 94 outwardly to the left, as shown in FIG. 8. The intravenous catheter placement needle tip 82 would then be withdrawn into the protective cap 94, much in the same manner as in the previously described embodiments.

If desired, a plurality of severable straps, such as thin straps 122, could extend between the body 74 or the hub 76 and the body 112 of the intravenous catheter assembly 110. In this way, the entire assembly would be held together for easy use and health professionals would only sever the straps after the intravenous catheter placement needle 80 has been inserted into a patient's body.

Figure 9:
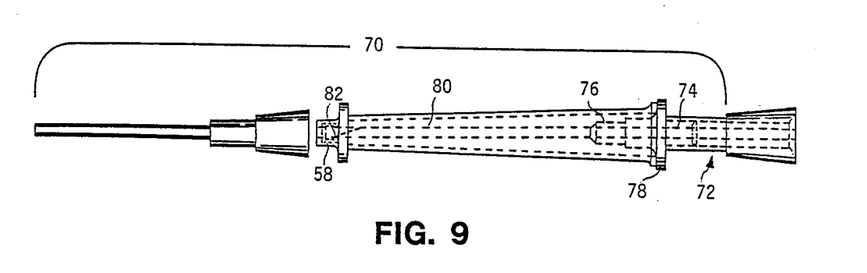
FIG. 9 is an exploded side elevational view in section, showing the intravenous catheter placement needle with a modified form of the protective device of the present invention used thereon.
Figure 10:
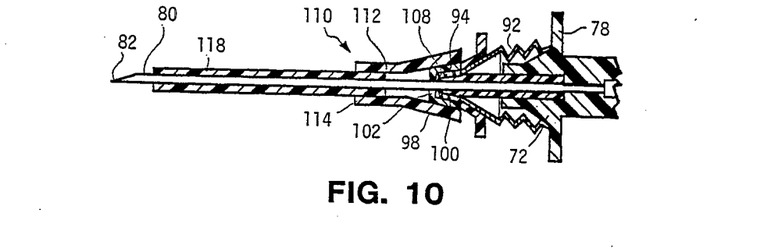
FIG. 10 is a sectional view of the assembly of FIG. 9 and showing the needle tip protective device in the compressed condition.

FIGS. 9 and 10 illustrate an embodiment of the invention which shows the use of a needle tip protective device in combination with an intravenous catheter placement needle and intravenous catheter arrangement similar to that previously described in connection with FIGS. 7 and 8 of the drawings. However, in the embodiment as illustrated in FIGS. 9 and 10, the intravenous catheter sleeve 92 is not tightly and snugly disposed about the shank of the intravenous catheter placement needle 80. Rather, in this embodiment of the invention, the right-hand end of this protective sleeve 92 is secured to the outwardly extending flange 78 in the manner as illustrated. Thus, the catheter sleeve is not secured to the intravenous catheter placement needle by the force of friction, but is held in place by its securement to the protective cap 94 at the left-hand end and its adhesive securement to the outwardly extending flange 78 at the right-hand end.

Again, this embodiment of the invention would normally be packaged in the compressed state as shown in FIG. 10. The assembly would be extended to its full length after successful placement of the intravenous catheter. The needle tip protective device would then be dismantled from the intravenous catheter housing. Beyond this, the needle tip protective device of the present invention works essentially in the same manner as the needle tip protective device illustrated and described in the embodiment of FIGS. 7 and 8 of the drawings.

Figure 11:
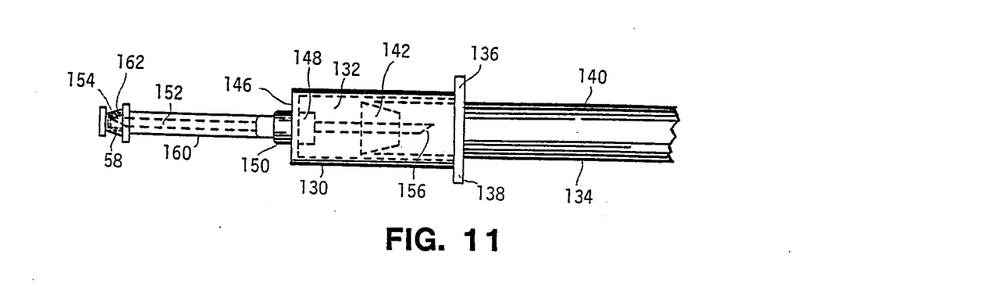
FIG. 11 is a side elevational view, showing the needle tip protective device of the present invention used with Vacutainer apparatus.

FIG. 11 is a vertical sectional view illustrating the use of the needle tip protective device in connection with a body fluid withdrawal apparatus of the type offered under the name "Vacutainer". In this case, the body fluid withdrawal device comprises a cylindrical housing 130 having an interior chamber 132 for receiving a body fluid sample tube, such as a blood sample tube 134. The sample tube 134 extends into the chamber 132 through an enlarged opening 136 at the right-hand end of the housing 130.

The sample tube 134 is of conventional construction and is comprised of an elongate tube body 140 having a stopper or plug 142 at its left-hand end. Moreover, the tube is evacuated so that a body fluid may be sucked into the tube 134 when the latter is connected to a body fluid source such as a blood vessel. The stopper 142 is formed of a material which forms an air tight seal at the left end of the sample tube 134, but which is still puncturable by a needle, as shown, and hereinafter described.

Secured to the left-hand flat end wall of 145 of the housing 130 is a hub 148 which threadedly accepts a threaded hub 150 of a Vacutainer needle 152. The needle 152 also terminates in a sharp left-hand end 154, as well as a sharp pointed right-hand end 156.

The hub 150 effectively carries the needle shank, which has sharp points at both of the opposite ends, as shown. Moreover, the hub is threaded, as aforesaid, to be removably attached to the fitting on the housing 130. The fitting is provided with an opening to receive the right-hand end of the needle, as shown. When the needle is assembled to the Vacutainer housing, the sharp tipped point 156 will penetrate through the plug 142 and access the interior of the sample tube 134. Since the left-hand end of the needle was previously inserted into a patient's body, the vacuum in the sample tube 134 will draw a sample of the body fluid.

The needle tip protective device also can be used with the Vacutainer apparatus, as illustrated in FIG. 11 of the drawings. In this case, it can be observed that the needle tip protective device comprises a sleeve 160, similar to the previously described sleeve 42 and a protective cap 152, similar to the previously described protective cap 46. In like manner, the protective cap 152 includes a sealing membrane (not shown) which is, again, similar to the previously described membrane or sealing member 58.

The needle tip protective device of FIG. 11 operates in essentially the same manner as the previously described needle tip protective devices in that the sharp tipped point 154 will remain within the protective cap 162 until an insertion is made into the patient's body. At this point, the protective sleeve 160 will collapse about the shank of the needle 152 into a series of wrinkles or convolutions as previously described. However, after withdrawal, the elastic nature of the protective sleeve will cause the cap 162 to move to the left and thereby again cover the sharp tipped point.

This use of the needle tip protective device of the present invention eliminates the need for the protective covers normally employed with Vacutainer needles and which are threadedly secured to both sides of the hub. Inasmuch as both ends of the needle are effectively enclosed when attached to a Vacutainer device and used with the instant needle tip protective device, there is no need for the normal protective covers.

Thus, there has been illustrated and described a unique and novel needle tip protective device which may be used with a wide variety of commercially available needle supports without requiring alteration of the support and which provides a universality of use for the needle tip protective device of the present invention. Accordingly, the present invention fulfills all of the objects and advantages which have been sought therefor. It should be understood that many changes, modifications, variations and other uses and applications will become apparent to those skilled in the art after considering this specification and the accompanying drawings. Therefore, any and all such changes, modifications, variations, and other uses and applications which do not depart from the spirit and scope of the invention are deemed to be covered by the invention which is limited only by the following claims.

Having thus described my invention, what I desire to claim and secure by letters patent is:

1. A needle tip protective device for use with a needle having a shank with a first end connected to a support and a second end having a sharp point capable of bodily insertion, said device comprising:
   (a) a resilient flexible sleeve capable of being disposed about the elongate shank of a needle and extending from the second end for at least the greater portion of the length of the shank toward the first end, said sleeve having an elongate central bore generally of constant and continuous cross-section throughout its length and capable of receiving the elongate shank of the needle and being concentrically disposed about said shank, at least a portion of said sleeve having an interior dimension and elasticity sufficient to cause the sleeve to snugly engage the outer wall of said needle and thereby retentively hold the protective device with respect to the needle and the support therefor, thereby avoiding the need for a special attachment means to attach the protective device to the support,
   (b) a cap secured to the second end of said sleeve and located to extend around and receive the second end of said needle, said cap having an enlarged opening through which said sharp point of the second end of said needle can extend, and
   (c) a sealing member normally extending across said enlarged opening and enclosing the sharp point of said second end of the needle within a chamber surrounding said needle and which chamber is formed by the central bore of said sleeve and said cap and protecting the user from the sharp point of the needle second end, said sharp point capable of extending through the sealing member when the needle is pushed against a skin surface and said sealing member is pushed against said sharp point causing the needle to extend through said sealing member and causing said sleeve to compress about said needle shank, said sleeve when compressed having sufficient elasticity to cause the sleeve to expand and extend about the full length of the needle thereby again enclosing the sharp point of the needle.

2. The needle tip protective device of claim 1 further characterized in that said central bore of the sleeve has a relatively constant shape throughout its length which conforms to the exterior surface of the needle.

3. The needle tip protective device of claim 2 further characterized in that said sleeve snugly engages the exterior surface of the needle for substantially the entire length of the needle.

4. The needle tip protective device of claim 1 further characterized in that said cap is formed of a plastic material and said sealing member is a membrane which extends across said enlarged opening and seals said sharp point of the needle within said cap.

5. The needle tip protective device of claim 1 further characterized in that said sealing member is a plug which is fitted within the enlarged opening of said cap and which has a puncturable portion axially aligned with said enlarged opening and is sized to receive the sharp point of the needle so that the point may be extended therethrough.

6. The needle tip protective device of claim 1 further characterized in that the portion of the sleeve snugly engaging the needle is proximate the second end of the needle.

7. The needle tip protective device a set forth in claim 1 further characterized in that said needle support defines a hypodermic needle body.

8. The needle tip protective device as set forth in claim 1 further characterized in that said needle support defines a Vacutainer needle body.

9. The needle tip protective device as set forth in claim 1 further characterized in that said needle support defines intravenous catheter placement needle body.

10. The needle tip protective device as set forth in claim 1 further characterized in that said cap is provided with outwardly extending rim at one end thereof.

11. The needle tip protective device a set forth in claim 10 further characterized in that said cap is provided with outwardly extending rim at the opposite end thereof.

12. The needle tip protective device as set forth in claim 1 further characterized in that the first end of the sleeve is diametrically larger than the first end of the needle and is secured to an outwardly extending rim on said support.

13. A needle tip protective device for use with an intravenous catheter placement needle assembly having a needle hub and an intravenous catheter tube and with the shank of the intravenous catheter placement needle connected to said hub and also having a sharp point capable of insertion into a body, said device comprising:
   (a) a resilient flexible sleeve capable of being disposed about the elongate shank of an intravenous catheter placement needle and extending over the greater portion of the length of the shank toward the intravenous catheter placement needle hub said sleeve having an elongate central bore generally of constant and continuous cross-section throughout its length capable of receiving the elongate shank of the needle and being concentrically disposed about said shank, at least a portion of said sleeve having an interior dimension and elasticity sufficient to cause the sleeve to be closely disposed about the outer wall of said intravenous catheter placement needle, said sleeve having one end adapted for attachment to said hub and thereby retentively hold the protective device with respect to the intravenous catheter placement needle.

(b) a cap secured to the opposite end of said sleeve and located to extend around and receive the second end of said intravenous catheter placement needle, said cap having an enlarged opening through which said sharp point of the end of said intravenous catheter placement needle can extend, and (c) a sealing member normally extending across said enlarged opening and enclosing the sharp point of said second end of the intravenous catheter placement needle within a chamber surrounding said intravenous catheter placement needle after intravenous catheter and withdrawal of the intravenous catheter placement needle, and which chamber is formed by the central bore of said sleeve and said cap and protecting the user from the sharp point of the intravenous catheter placement needle second end.

14. The needle tip protective device of claim 13 further characterized in that said sleeve snugly engages the exterior surface of the hub.

15. A needle tip protective device for use with an intravenous catheter placement needle assembly having a needle support and an intravenous catheter tube, and with the shank of the intravenous catheter placement needle connected to said support, and also having a sharp point capable of insertion into a body, said device comprising:

(a) a resilient flexible sleeve capable of being disposed about the elongated shank of a needle and extending from the first end for at least the greater portion of the length of the shank toward the second end, said sleeve having a central bore generally decreasing in capacity downward, receiving the elongate shank of the needle and being diametrically disposed about said shank having a significant interior dimension not tightly or snugly disposed about the shank of the intravenous catheter needle, said sleeve having one end adhesively secured or the like for permanent attachment to said needle support, said sleeve extending over said support thereby requiring the need for a special attachment means to secure the protective device to the support, (b) a cap formed of a material more rigid than said sleeve secured to the opposite end of said sleeve and located to extend around and receive the second end of said intravenous catheter placement needle after implantation of an intravenous catheter, said cap having an enlarged opening through which said sharp point of the second end of said intravenous catheter placement needle can extend, and formed with an outwardly extending rim and an inwardly tapering portion projecting forwardly from said rim configured to mate within the body portion of an intravenous catheter to be extended through said cap and intravenous catheter for implantation of said catheter in a patient, (c) a sealing member normally extending across said enlarged opening of said cap and enclosing the sharp point of said second end of the intravenous catheter placement needle within a chamber surrounding said intravenous catheter placement needle and which chamber is formed by the central bore of said sleeve and said cap protecting the user from the sharp point of the needle second end, said sharp point capable of extending through the sealing member and intravenous catheter tube before the implantation of the catheter, when the intravenous catheter placement needle is pushed into the wall of a blood vessel causing the catheter to be implanted into the patient, causing said sharp point to be withdrawn, after implantation of said catheter, through said sealing member and causing said sleeve to extend about the full length of the needle thereby again enclosing the sharp point of the needle protecting the user from the sharp point of the intravenous catheter placement needle second end.

16. The needle tip protective device as set forth in claim 15 further characterized in that the first end of the sleeve is diametrically large than the first end of the needle shaft and is secured to an outwardly extending rim on said support.

17. The needle tip protective device as set forth in claim 15 further characterized in that said cap is formed of a plastic material and said sealing member is a membrane which extends across said enlarged opening and seals said sharp point of the needle within said cap.

18. The needle tip protective device as set forth in claim 17 further characterized in that said cap is provided with an outwardly extending rim at one end thereof.

19. The needle tip protective device as set forth in claim 18 further characterized in that said cap is provided with a tapering portion projecting forwardly from said outwardly extending rim at the opposite end thereof.

* * * * *